(12) United States Patent
Matsumoto et al.

(10) Patent No.: US 6,327,375 B1
(45) Date of Patent: *Dec. 4, 2001

(54) OPHTHALMOLOGIC PHOTOTAKING APPARATUS

(75) Inventors: Kazuhiro Matsumoto, Yono; Takashi Masuda, Yamato; Takeshi Kitamura, Utsunomiya; Motoya Takai, Kawasaki; Hiroshi Nishihara; Tetsuji Ogawa, both of Utsunomiya, all of (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,304

(22) Filed: Jun. 17, 1997

(30) Foreign Application Priority Data

Jun. 17, 1996 (JP) ........................................... 8-177096

(51) Int. Cl.⁷ ............................. G06K 9/00; A61B 3/10
(52) U.S. Cl. ......................... 382/117; 382/239; 351/211; 351/221
(58) Field of Search ........................... 382/117, 239; 351/211, 212, 221; 128/670

(56) References Cited

U.S. PATENT DOCUMENTS

| | | | |
|---|---|---|---|
| 4,660,946 | 4/1987 | Nakamura et al. | 351/212 |
| 4,710,003 | 12/1987 | Masuda et al. | 351/212 |
| 4,755,041 | 7/1988 | Ishikawa et al. | 351/211 |
| 4,764,006 | 8/1988 | Hamano | 351/211 |
| 4,820,037 | 4/1989 | Kohayakawa et al. | 351/211 |
| 4,825,296 | * 4/1989 | Wagensonner et al. | 358/280 |
| 4,848,896 | 7/1989 | Matsumoto | 351/211 |
| 4,952,049 | 8/1990 | Matsumoto | 351/211 |
| 5,237,351 | 8/1993 | Kohayakawa et al. | 351/243 |
| 5,302,979 | 4/1994 | Maeda et al. | 351/212 |
| 5,455,644 | 10/1995 | Yazawa et al. | 351/206 |
| 5,500,696 | 3/1996 | Masuda et al. | 351/205 |
| 5,530,494 | 6/1996 | Ogawa et al. | 351/206 |
| 5,553,160 | * 9/1996 | Dawson | 382/166 |
| 5,701,904 | * 12/1997 | Simmons et al. | 128/670 |
| 5,751,396 | * 5/1998 | Masuda et al. | 351/221 |

OTHER PUBLICATIONS

JP402243082A, Matsuo, Chikao, et al. "Picture Data Transmitting Device", 1990.*

Dutendas, D. et al., "Unsupervised Bayesian Segmentation With Bootstrap Sampling Application to Eye Fundus Image Coding", IEEE, 1995, pp 1794–1796.*

* cited by examiner

Primary Examiner—Matthew C. Bella
(74) Attorney, Agent, or Firm—Fitzpatrick, Cella, Harper & Scinto (57) ABSTRACT

The present invention relates to an ophthalmologic phototaking apparatus having an illuminating system for illuminating an eye to be examined, a phototaking system for phototaking the image of the eye to be examined illuminated by the illuminating system, a digital signal converting system for converting the image of the eye to be examined phototaken by the phototaking system into a first data format of digital image data, and a data format converting system for converting the first data format of digital image data into a second data format of digital image data.

4 Claims, 6 Drawing Sheets

OPHTHALMOLOGIC PHOTOTAKING APPARATUS

BACKGROUND OF THE INVENTION

1. Field of the Invention

This invention relates to an ophthalmologic phototaking apparatus capable of outputting the image of an eye to be examined as a digital signal.

2. Related Background Art

There is known an ophthalmologic phototaking apparatus system in which a TV camera having an analog image signal output is connected to an ophthalmologic phototaking apparatus body to thereby phototake the image of an eye to be examined and an analog image signal obtained can be outputted to a surrounding apparatus. However, the system outputting an analog image signal is weak against disturbance and suffers from the disadvantage that deterioration occurs to the image before diagnosis.

So, in recent years, use has generally been made of an ophthalmologic phototaking system in which a digital camera having a digital image signal output is connected to an ophthalmologic phototaking apparatus body and a digital image signal obtained with the phototaken image of an eye to be examined can be outputted to a surrounding apparatus such as an image recording apparatus. There is also known an ophthalmologic phototaking system which can output phototaking condition information and information relating to an eye to be examined such as patient information from output means differing from an image signal output means.

There is further known an ophthalmologic phototaking apparatus in which an electronically phototaken image is converted into digital data and is transferred to the outside and recorded on a portable type recording medium, and the rate of image compression is preselected before a series of phototaking operations are performed, and the image is compressed in conformity with the compression rate and is recorded on a recording medium.

(1) However, in the ophthalmologic phototaking apparatus according to the above-described example of the conventional art, the data of the digital image signal outputted from the digital camera adopts a form in which the information of each pixel is simply outputted, and the size of the image, the amount of information in the direction of harmony and the kind of the image such as whether the image is a colored image differ from one type of machine to another and therefore, the form of the outputted data is unique to the type of machine. Therefore, the surrounding apparatus receiving the digital image signal output must prepare exclusive data converting means in conformity with the type of the digital camera. Accordingly, the surrounding apparatus is limited to exclusive use with the ophthalmologic phototaking apparatus and has not the interchangeability with other diagnosis systems in the hospital, and this leads to the problem that the ophthalmologic phototaking apparatus becomes an ophthalmologic phototaking apparatus system of low flexibility.

(2) Also, the apparatus designed such that the compression rate of the image is set by outside recording means has the problem that it is difficult to set the compression rate in the course of a group examination or in the course of the fluorescent retinal phototaking operation and setting is liable to be forgotten because the setting conditions cannot be confirmed. Further, the eye fundus camera body is not provided with means for detecting the image compression information to be phototaken from now on and therefore, in spite of the information being lost by image compression, a light brighter than necessary is applied to the eye to be examined and phototaking is effected with a low gain in order not to deteriorate the S/N ratio. Also, the current image is not preserved for generally non-reversible image compression, and this leads to the problem that re-compression cannot be done and the quality of image as a further compressed result cannot be confirmed on the spot.

(3) Further, the information relating to the eye to be examined and the image signal of the eye to be examined are outputted from discrete means at different timings and therefore, there is the possibility that the discordance of data that the information relating to the eye to be examined and the image information do not coincide with each other may occur.

(4) Also, when the digital signal is outputted, there are present numerous different data forms for communication and output means which prescribe the communication speed, the input and output terminals and the communication form such as either serial or parallel, and this leads to the problem that great limitations are given to the surrounding apparatus.

SUMMARY OF THE INVENTION

It is an object of the present invention to solve the above-noted problem (1) and to provide an ophthalmologic phototaking apparatus which does not require any special data converting means on the surrounding apparatus side, which is excellent in flexibility and which is strong to disturbance and is high in the quality of image.

It is another object of the present invention to solve the above-noted problem (2) and to provide an ophthalmologic phototaking apparatus which can confirm the quality of a compressed image even in the course of phototaking and effect the re-selection of the compression rate.

It is still another object of the present invention to solve the above-noted problem (3) and to provide an ophthalmologic phototaking apparatus which prevents the discordance of data and which is high in reliability.

It is yet still another object of the present invention to solve the above-noted problem (4) and to provide an ophthalmologic phototaking apparatus which can cope with a wide range of surrounding apparatus without being affected by a variety of data forms for communication differing in diagnosis system from one another and output means.

Further objects of the present invention will become apparent from the following detailed description of some embodiments of the invention.

DESCRIPTION OF THE PREFERRED EMBODIMENTS

The present invention will hereinafter be described in detail with respect to some embodiments thereof shown in the drawings.

Figure 1:
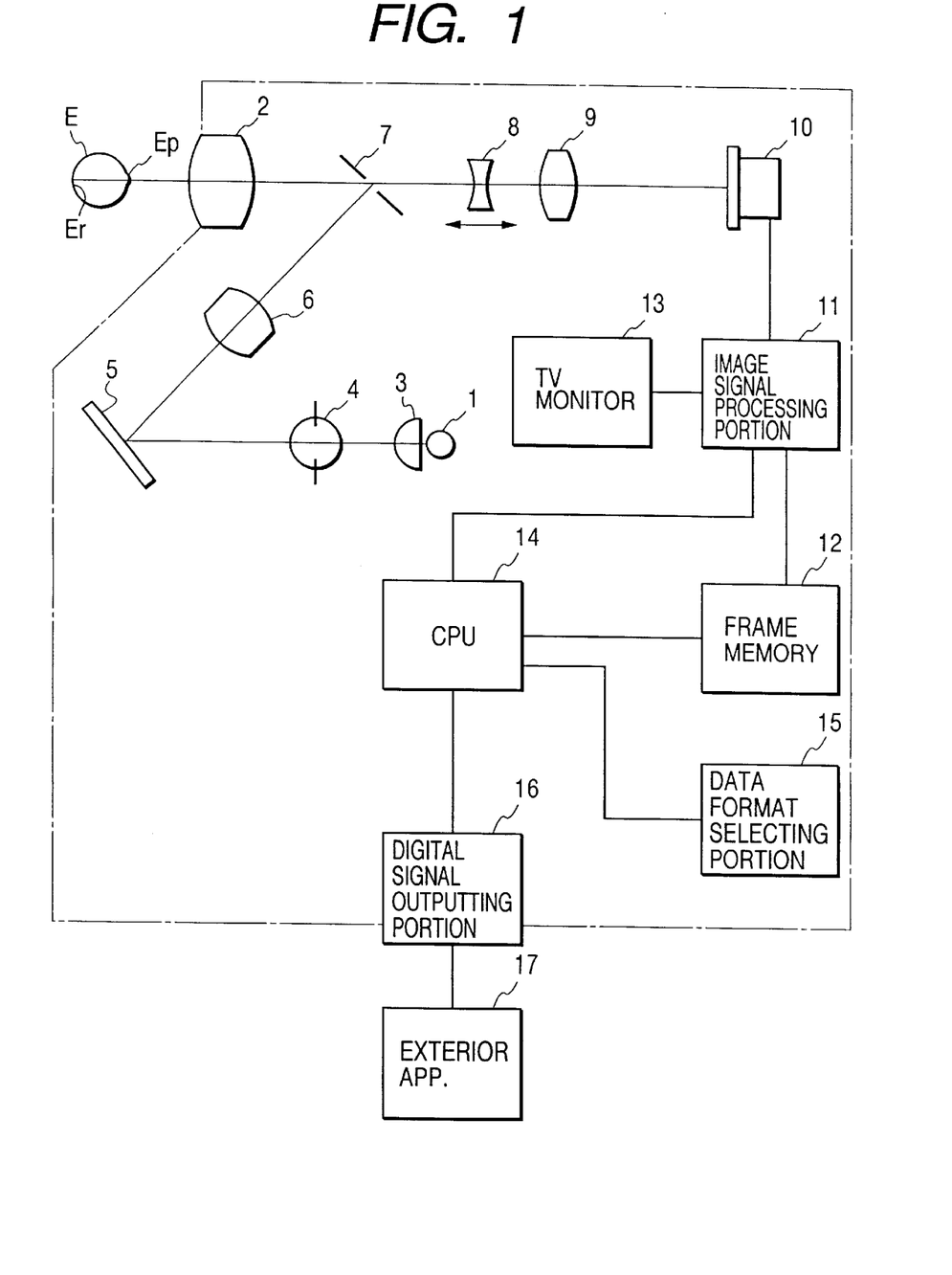
FIG. 1 shows the construction of a first embodiment of the present invention.

Referring to FIG. 1 which shows the construction of an eye fundus camera according to a first embodiment of the present invention, a condenser lens 3, a light source 4 for phototaking, a mirror 5, a relay lens 6 and an apertured mirror 7 are successively arranged on an optical path leading from a light source 1 for observation to an objective lens 2, and a focusing lens 8, a phototaking lens 9 and an image pickup element 10 are arranged on an optical path rearward of the apertured mirror 7. The output of the image pickup element 10 is connected to an image signal processing portion 11, the output of which is connected to a frame memory 12, a TV monitor 13 and a CPU (central processing unit) 14. The outputs of the frame memory 12 and a data format selecting portion 15 are connected to the CPU 14, the output of which is connected to an exterior apparatus 17 through a digital signal outputting portion 16. In the present embodiment, data format converting means is provided as a part of the function of the CPU 14.

A light beam emitted from the light source 1 for observation passes through the condenser lens 3, the mirror 5 and the relay lens 6, is reflected by the peripheral portion of the apertured mirror 7, passes through the objective lens 2 and the pupil Ep of an eye E to be examined and illuminates the fundus Er of the eye. The image of the illuminated fundus of the eye passes through the pupil Ep of the eye E to be examined, the objective lens 2 and the aperture in the apertured mirror 7, passes through the focusing lens 8 and the phototaking lens 9 and is imaged on the image pickup element 10. The image of the fundus of the eye formed on the image pickup element 10 is processed by the image signal processing portion 11 and is displayed on the TV monitor 13.

An examiner effects alignment while looking at the image on the TV monitor 13, and when he depresses a phototaking switch, not shown, when the alignment has been done, the input of the phototaking switch is detected by the CPU 14. The CPU 14 causes the light source 4 for phototaking to unit light through a light source control portion, not shown, while taking synchronism with the image signal processing portion 11.

A light beam emitted from the light source 4 for phototaking travels along an optical path similar to that of the above-described observation light and arrives at the fundus Er of the eye E to be examined, and the image of the fundus of the eye is directed to the image pickup element 10 in a similar manner. The CPU 14 transmits the timing at which the light source 4 for phototaking is caused to emit light to the image signal processing portion 11, which thus converts the signal from the image pickup element 10 into a digital signal on the basis of this timing, and starts to write into the frame memory 12.

At a point of time whereat the image of the fundus of the eye E to be examined obtained by the light emission of the light source 4 for phototaking has been recorded in the frame memory 12, the image signal processing portion 11 transmits the completion of the recording to the CPU 14. Here, the CPU 14 is in a state in which it can communicate with the exterior apparatus 17 through the digital signal outputting portion 15. The CPU 14 which has received the completion of the recording from the image signal processing portion 11 repeats the process of converting the data format and writing it into the frame memory 12 while reading out the digital image signal stored in the frame memory 12.

The data format converting process converts the data format into a universal image data format specifically represented by TIFF (tag image file format) or the like, and is achieved by a method of describing all of the size of the image calculated by the image pickup element of a camera which has picked up an image, the resolving power in the direction of harmony determined by the image signal processing portion 11 and detailed information about the image as to whether the image is a colored image by the image pickup element as data in the first portion of the image data, and thereafter adding a digital image signal conforming to the detailed information.

The data format selecting portion 15 may be provided to enable an operator to select a data format, and design may be made such that the data format to be converted is determined in response to the input from the data format selecting portion 15.

The CPU 14 reads the data after the termination of the data format converting process written into the frame memory 12, and outputs it to the exterior apparatus 17 through the digital signal outputting portion 16. The exterior apparatus can evolve the received digital image signal in accordance with the detailed information about the image described in the first portion and execute reproduction, and when recording, the exterior apparatus 17 can intactly record the received digital image signal on a recording medium without effecting the conversion or the like of the data format. In this manner, there can be achieved an ophthalmologic phototaking system excellent in universal use which does not give limitations to the exterior apparatus.

Figure 2:
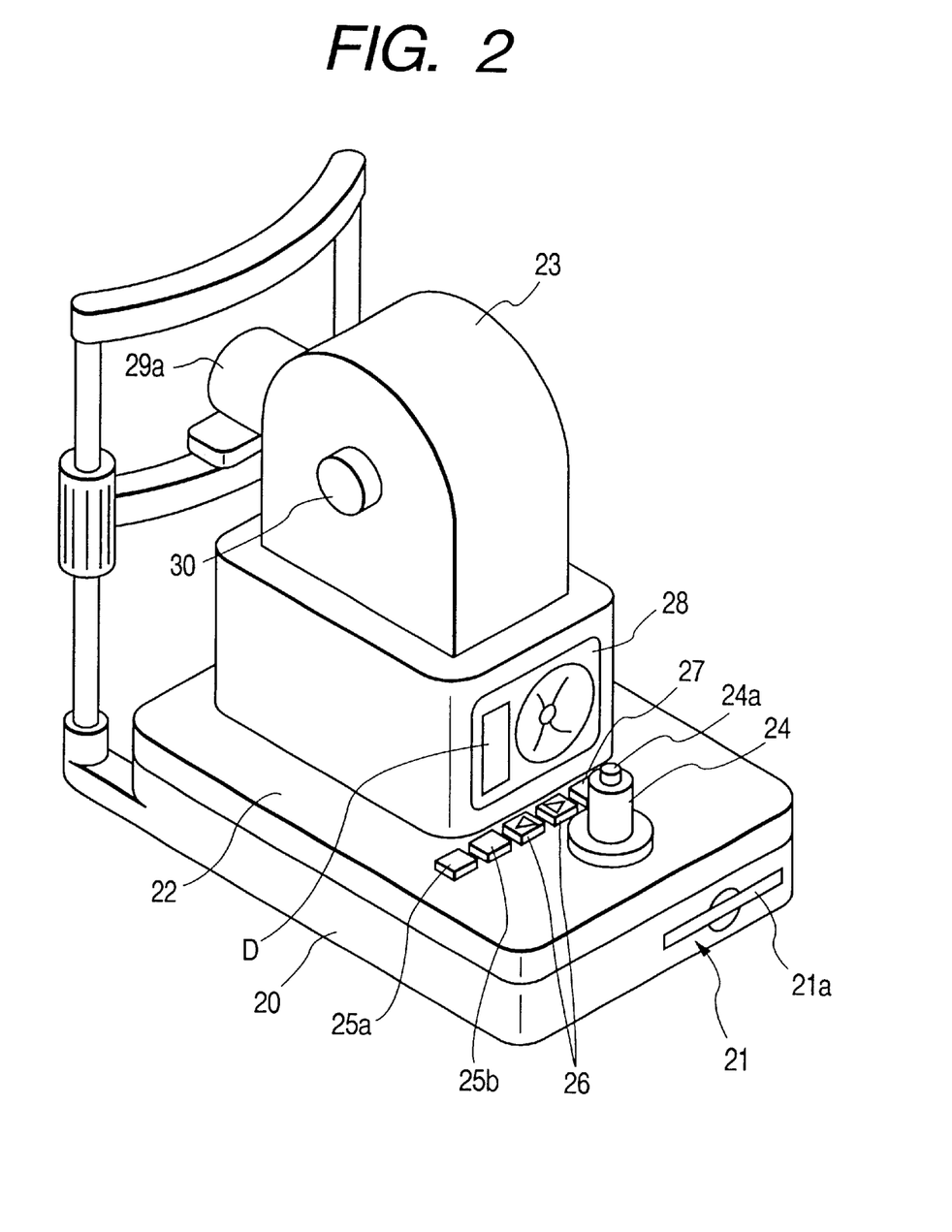
FIG. 2 is a perspective view of a second embodiment of the present invention.

Referring to FIG. 2 which is a perspective view of an eye fundus camera according to a second embodiment of the present invention, R/W recording means 21 for effecting the writing-in and reading-out of information with a portable type recording medium 21b such as MO or MD inserted into a slot 21a is provided on that side of a base 20 which is adjacent to a photographer. Also, a movable stage portion 22 is placed on the base 20, and the measuring portion body 23 of the eye fundus camera is provided on that side of the movable stage portion 22 which is adjacent to an examinee, and an operating rod 24 having a phototaking switch 24a on the upper portion thereof, selecting switches 25a and 25b for selecting the execution of the preservation or the permission for the erasing of the image, compression rate selecting means 26 for effecting the setting of a compression rate, a mode selecting switch 27 for selecting the before-phototaking setting mode and the after-phototaking setting mode, etc. are disposed on that side of the movable stage portion 22 which is adjacent to the photographer. Design is made such that in the case of the before-phototaking setting mode, the image is compressed in operative association with phototaking at a compression rate set before phototaking, and is preserved in the recording medium 21b, and in the case of the after-phototaking setting mode, the quality of the image phototaken is confirmed after phototaking and a compression rate is selected.

A TV monitor 28 is provided on that side of the measuring portion body 23 which is adjacent to the photographer, and a display portion for the image E' of the fundus of the eye and a display portion D for displaying the mode selected during phototaking, a target compression rate and information such as the number of remaining photographable frames are provided on the screen of the TV monitor 28. Also, a lens barrel 29a containing an objective lens 29 therein is fixed to that side of the measuring portion body 23 which is adjacent to the examinee, and focus adjusting means 30 comprising a focusing knob is provided on a side of the measuring portion body 23, and the other optical members are contained in the measuring portion body 23.

Figure 3:
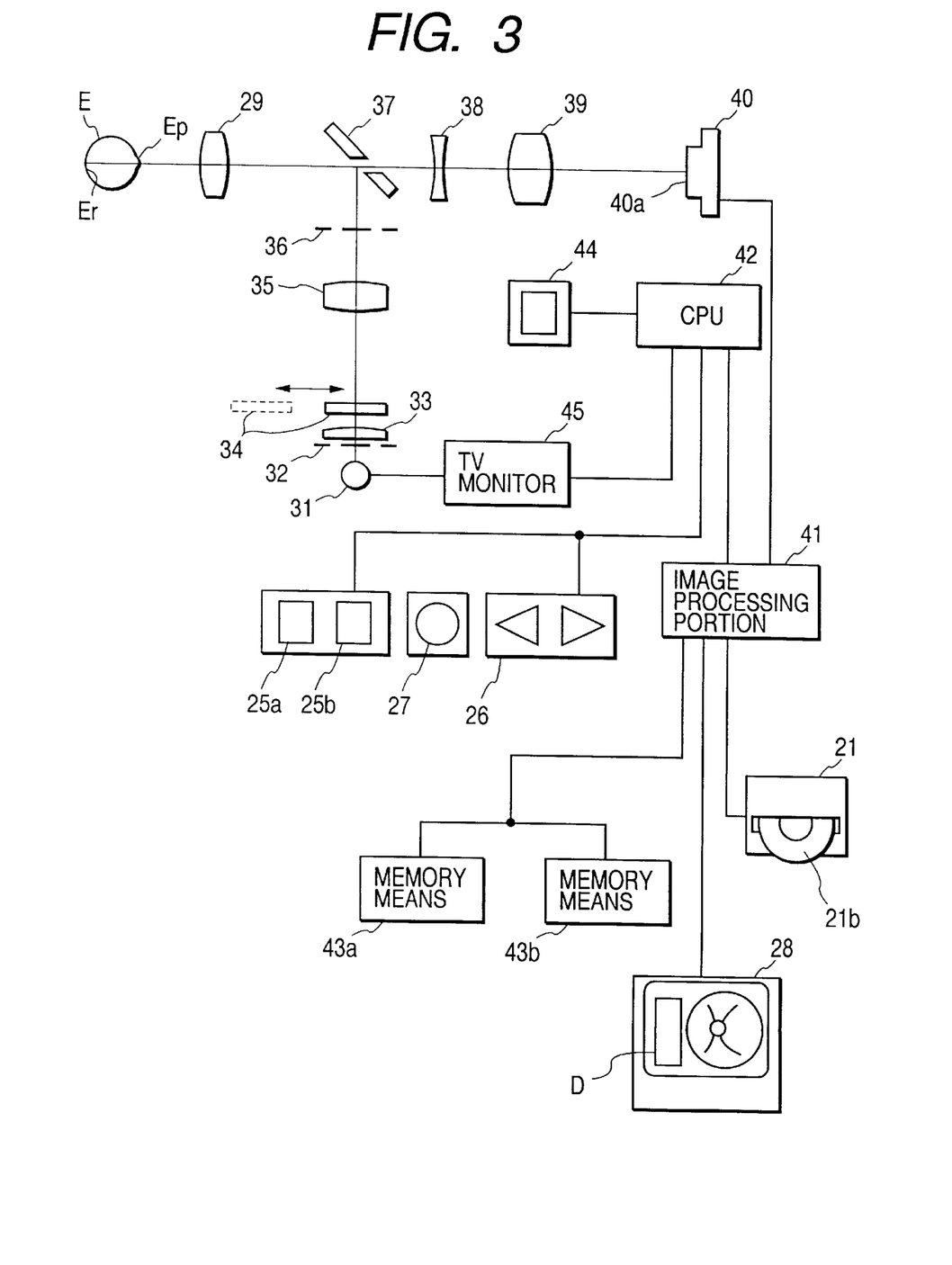
FIG. 3 shows the construction of the second embodiment.

Referring to FIG. 3 which shows the construction of the second embodiment, a stop 32 having a ring-shaped opening, a lens 33, a removably insertable infrared filter 34 intercepting visible light and passing only infrared light therethrough, a relay lens 35, a stop 36 having a ring-shaped opening, and an apertured mirror 37 are successively arranged on an optical path leading from a light source 31 for observation and phototaking such as a lamp to the objective lens 29. A focusing lens 38 for effecting focusing, a phototaking lens 39 and image pickup means 40 which is a camera for observation and phototaking such as a two-dimensional CCD and which is capable of color-phototaking for visible light are successively arranged on an optical path rearward of the apertured mirror 37.

The output of the image pickup means 40 is connected to an image processing portion 41 having the function of converting the signal from the image pickup means 40 into a digital signal and the function of converting digital data into an analog signal and producing an image signal, and the output of the image processing portion 41 is connected to a CPU 42, the TV monitor 28, the R/W recording means 21 and memory means 43a and 43b storing therein image data and calculation data, respectively. Also, the outputs of the selecting switches 25a, 25b, the compression rate selecting means 26, the mode selecting switch 27 and a phototaking switch 44 are connected to the CPU 42, the output of which is connected to light emission control means 45 for the light source 31 for observation and phototaking.

In such a construction, a light beam emitted from the light source 31 for observation and phototaking passes through the opening in the stop 32 and the lens 33, has its visible light component removed by the infrared filter 34, passes through the lens 35 and the opening in the stop 36, is leftwardly reflected by the mirror portion of the apertured mirror 37, further passes through the objective lens 29 and illuminates the pupil Ep to the fundus Er of an eye E to be examined. The thus illuminated image of the fundus of the eye passes through the pupil Ep, the objective lens 29, the aperture portion of the apertured mirror 37, the focusing lens 38 and the phototaking lens 39, and is imaged on the image pickup surface 40a of the image pickup means 40. This image is then converted into an electrical signal, which is inputted to the image processing means 41 and the image of the fundus of the eye is displayed on the TV monitor 28.

The photographer looks at the image of the fundus of the eye displayed on this TV monitor 28 and confirms the phototaken region, alignment and the state of focusing, and when the focusing is not good, the photographer position-adjusts the focusing lens 38 in the direction of the optical axis thereof by the use of the focus adjusting means 30. Then the photographer confirms in the image of the fundus of the eye displayed on the TV monitor 28 that the focusing is good, whereafter the photographer operates the phototaking switch 44 to thereby execute phototaking. At this time, the light emission control means 45 increases the quantity of light emitted from the light source 31 for observation and phototaking, and the infrared filter 34 comes off the optical path and the image pickup means 40 starts accumulation for still picture phototaking.

Thereby, visible light passes through the lens 35 and the opening in the stop 36 is leftwardly reflected by the mirror portion of the apertured mirror 37, passes through the objective lens 29 and illuminates the pupil Ep to the fundus Er of the eye E to be examined. The thus illuminated image of the fundus of the eye passes through the pupil Ep, the objective lens 29, the aperture portion of the apertured mirror 37, the focusing lens 38 and the phototaking lens 39 and is formed on the image pickup surface 40a of the image pickup means 40. The image data outputted from the image pickup means 40 is A/D-converted by the image processing means 41, and is stored in the memory means 43a and thereafter is displayed on the TV monitor 28.

Looking at this image, the photographer selects by the selecting switches 25a, 25b whether to effect image compression and preserve the image or to store the original image as it is, and for example, when there is obtained an image of high contract to the details, the photographer selects a compression rate 1/1 by the compression rate selecting means 26 and executes preservation by the preservation switch 25a. Thereby, the image data is stored intactly as the original image in the portable type memory medium 21b by the R/W means 21.

Also, when the examinee has the opacity of the eye anterior portion such as cataract and an image of high contract could be obtained or the state of the dilation of the pupil of the examinee's eye is not sufficient and some area of the image has become dark, a desired compression rate, e.g. 1/10, is selected by means of the compression rate selecting means 26. Thereupon, an image compressed to 1/10 is displayed on the monitor 28, and if there is no problem in that compression rate, preservation is executed by means of the preservation switch 25a. In this manner, image compression can be done in a state in which the deterioration of the quality of image is little.

Figure 4:
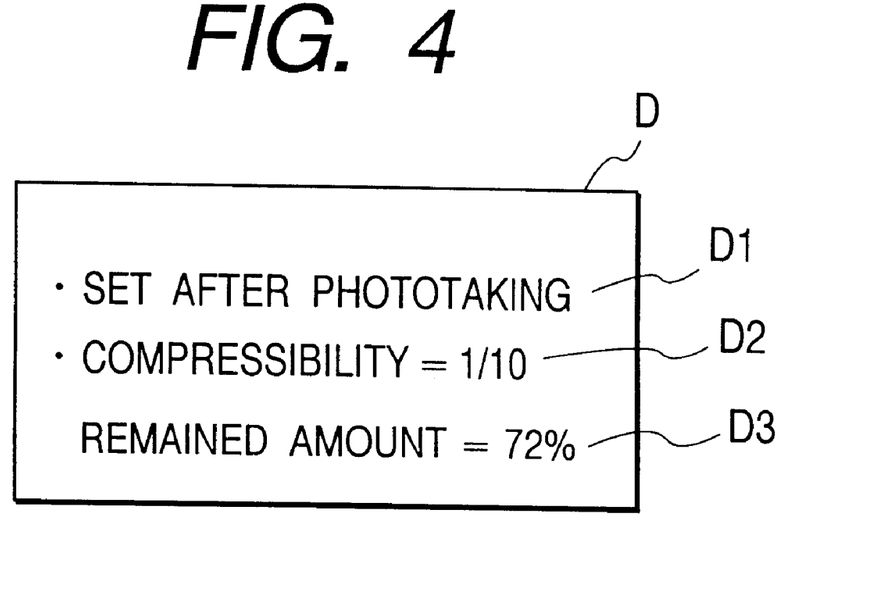
FIG. 4 is an illustration of display means.
Figure 5:
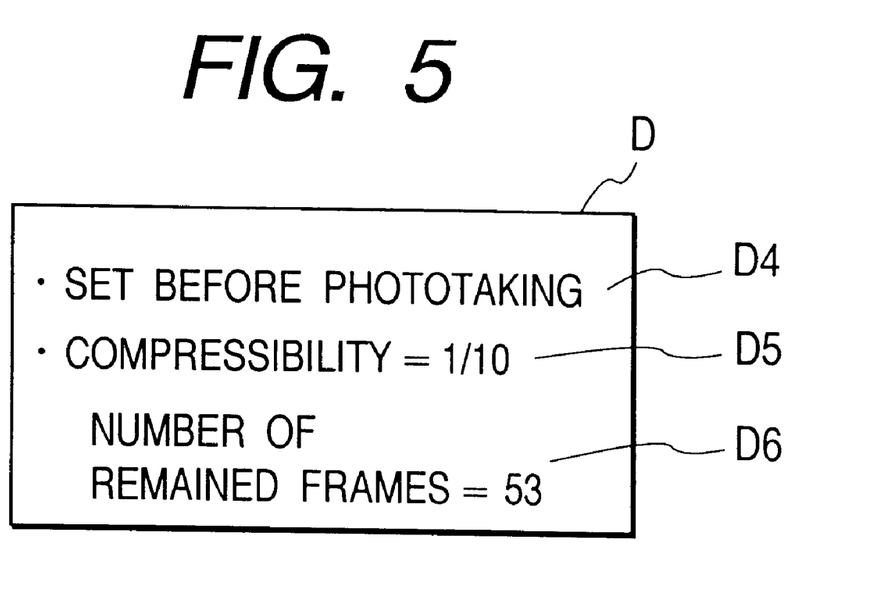
FIG. 5 is an illustration of the display means.

At this time, as shown in FIG. 4, the set mode display after phototaking D1, the target compressibility display D2, the number of photographable remaining frames D3, etc. are displayed on the display portion D of the TV monitor 28, and the image data is image-compressed and recorded on the portable type storing medium 21b by the R/W recording means 21. When the current image is to be preserved as it is, the compressibility display D2 is displayed as ¼.

When a sufficient quality of image is not obtained and the image obtained is not worth preservation or when it is judged that re-phototaking is necessary, the erasing permitting switch 25b is operated and re-phototaking is done. If thus the erasing permitting switch 25b is provided and design is made such that the next phototaking is prohibited until the photographer selects preservation or erasing permission, the accident that the phototaken image is inadvertently erased can be prevented.

Also, when the TV monitor 28 used is simple display means such as a small Braun tube or a liquid crystal display device which cannot reproduce all of image infirmation, if the compressed image data is once stored in the memory 43b and that image is expanded by the image processing portion 41 and is displayed on the TV monitor 28, the compression rate can be selected while the quality of image is confirmed and therefore, the photographer becomes able to select the optimum compression rate easily and without losing necessary information, and can efficiently utilize the R/W recording means 21. If at this time, a plurality of screens can be multiwindow-displayed on the TV monitor 28 and the compressed image is displayed with the original image, the confirmation of the quality of image can be done more easily and the phototaking efficiency can be improved.

When the set mode before phototaking is to be selected, the operation of the preservation switch 25a is not necessary, and the image is automatically compressed at a preset compression rate with phototaking and is recorded on the portable type recording medium 21b. If this is done, the image at a required compression rate can be recorded simply by performing the phototaking operation and therefore, phototaking can be accomplished efficiently and purposefully.

As another embodiment, the reference voltage and the quantity of phototaking light when the image signal from the image pickup means 40 is A/D-converted may be changed over in accordance with the compression rate set before phototaking, whereby the phototaking condition such as the quantity of light applied to the eye E to be examined or the allowed amount of focusing may be changed. Generally, when image compression is done, the high frequency component of the image is removed and therefore, an image compressed and preserved becomes greater in S/N ratio than an image preserved without being compressed. Accordingly, if the compression rate for preservation is determined before phototaking, means for changing the amplification factor of the signal from the image pickup means 40 can be provided and the amplification factor can be made greater in accordance with the compression rate and along therewith, the quantity of light applied to the eye E to be examined can be decreased.

In this case, the CPU 42 detects, before phototaking, the compression rate at which the image is compressed after phototaking, and calculates the amplification factor of the image signal or the accumulation time and the quantity of emitted light of the image pickup means 40, and on the basis of the result of this calculation, the light emission control means 45 controls the light emission of the light source 31 for observation and phototaking during the inputting of the phototaking switch 44. A similar operation is also possible by changing the reference voltage when A/D conversion is done.

Also, if auto-focus means or means for displaying the in-focus is provided, the allowed amount for recognizing the in-focus can be made greater with the compression rate to thereby shorten the time until phototaking is permitted, and more efficient phototaking can be accomplished.

Also, in the ophthalmologic phototaking apparatus, there are various forms of phototaking such as color phototaking, infrared phototaking, visible fluorescent phototaking and infrared fluorescent phototaking, but the characteristic required of an image picked up differs from one form of phototaking to another and therefore, if design is made such that when the compression is selected by the compression rate selecting switch 26, the target compression rate is automatically set in conformity with the form of phototaking, the portable type recording medium 21b can be utilized more efficiently.

In the present embodiment, the display portion for the image E' of the fundus of the eye and the display portion D for displaying various kinds of information are provided in the screen of the TV monitor 28, but alternatively, the information displayed on the display portion D may be displayed on another display means. Further, the screen of the TV monitor 28 may be changed over so that the image E' of the fundus of the eye and the information on the display portion D may be displayed discretely from each other.

Also, if an index image compressed at a great compression rate such as 1/50 discretely from the compression rate set by the photographer is stored at the same time, this index image does not take such time to transfer and read out the image and therefore, it becomes unnecessary to read out much information in order to confirm the contents of the recording medium after phototaking and retrieval becomes easy.

Figure 6:
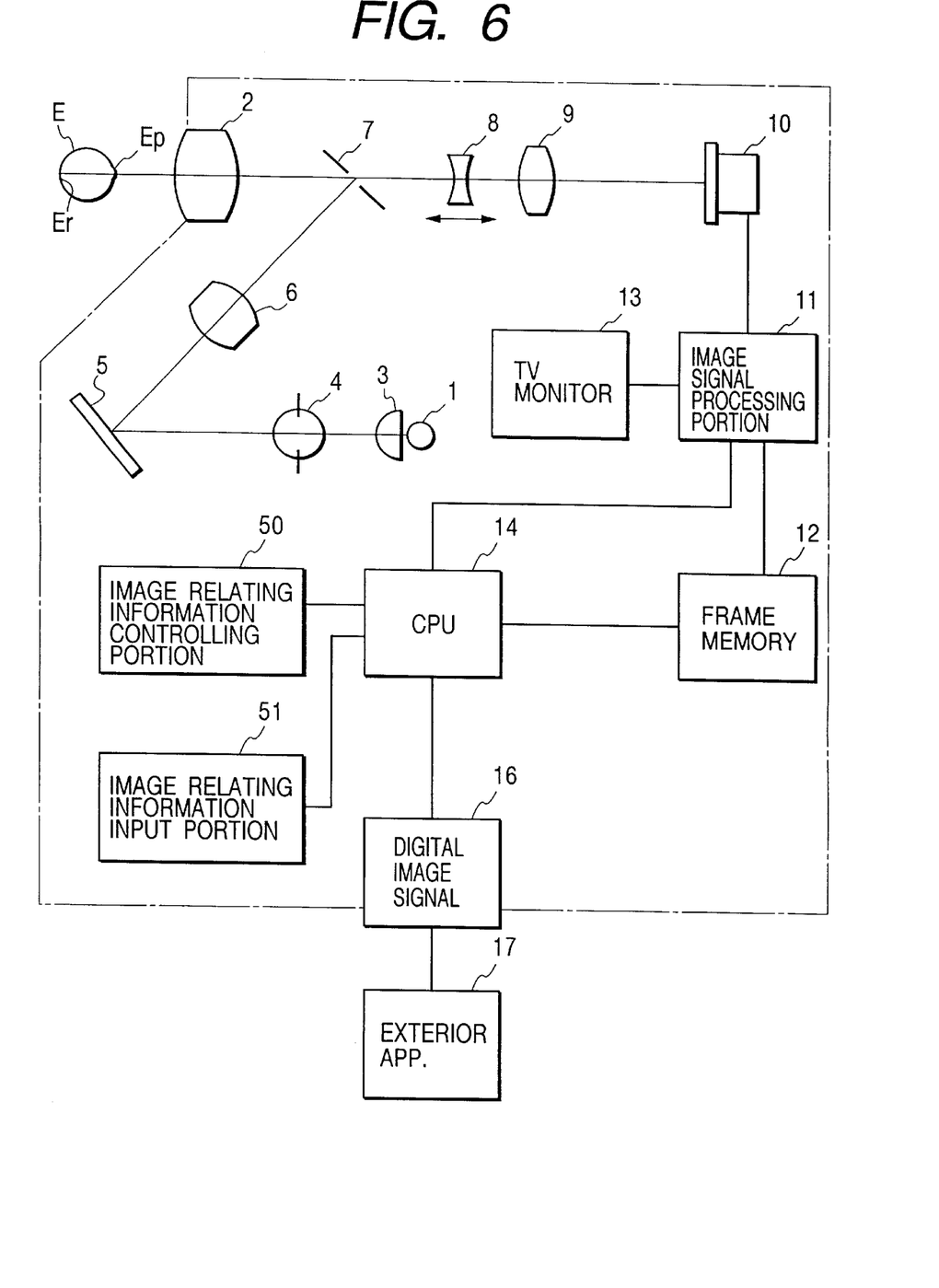
FIG. 6 shows the construction of a third embodiment of the present invention.

Referring now to FIG. 6 which shows the construction of a third embodiment of the present invention, this embodiment is of a construction in which the data format selecting portion 15 of FIG. 1 is eliminated and an image relating information controlling portion 50 and an image relating information input portion 51 are added. The output of the image relating information input portion 51 which is input means for patient's name, patient's number, etc. is connected to the CPU 14, the output of which is connected to the image relating information controlling portion 50 for effecting the storage and controlling of relating information.

The CPU 14 outputs to the image relating information controlling portion 50 the patient information such as patient's name, patient's number and special items inputted from the image relating information input portion 51, and the phototaking conditions such as the angle of view of phototaking, the quantity of emitted light and the discrimination between right and left from a phototaking condition outputting portion, not shown. When an image is recorded in the frame memory 12 by the phototaking operation shown in the first embodiment, the CPU 14 reads out the image relating information such as patient information and phototaking condition from the image relating information controlling portion 50 and reads out a digital image signal from the frame memory 12, and combines these two types of information together and outputs them as a series of data to the exterior apparatus 17 through the digital signal outputting portion 16. In this manner, there can be achieved a system in which the digital image signal and the image relating information are outputted from a single output means and the discordance of data does not occur and which is excellent in reliability.

Figure 7:
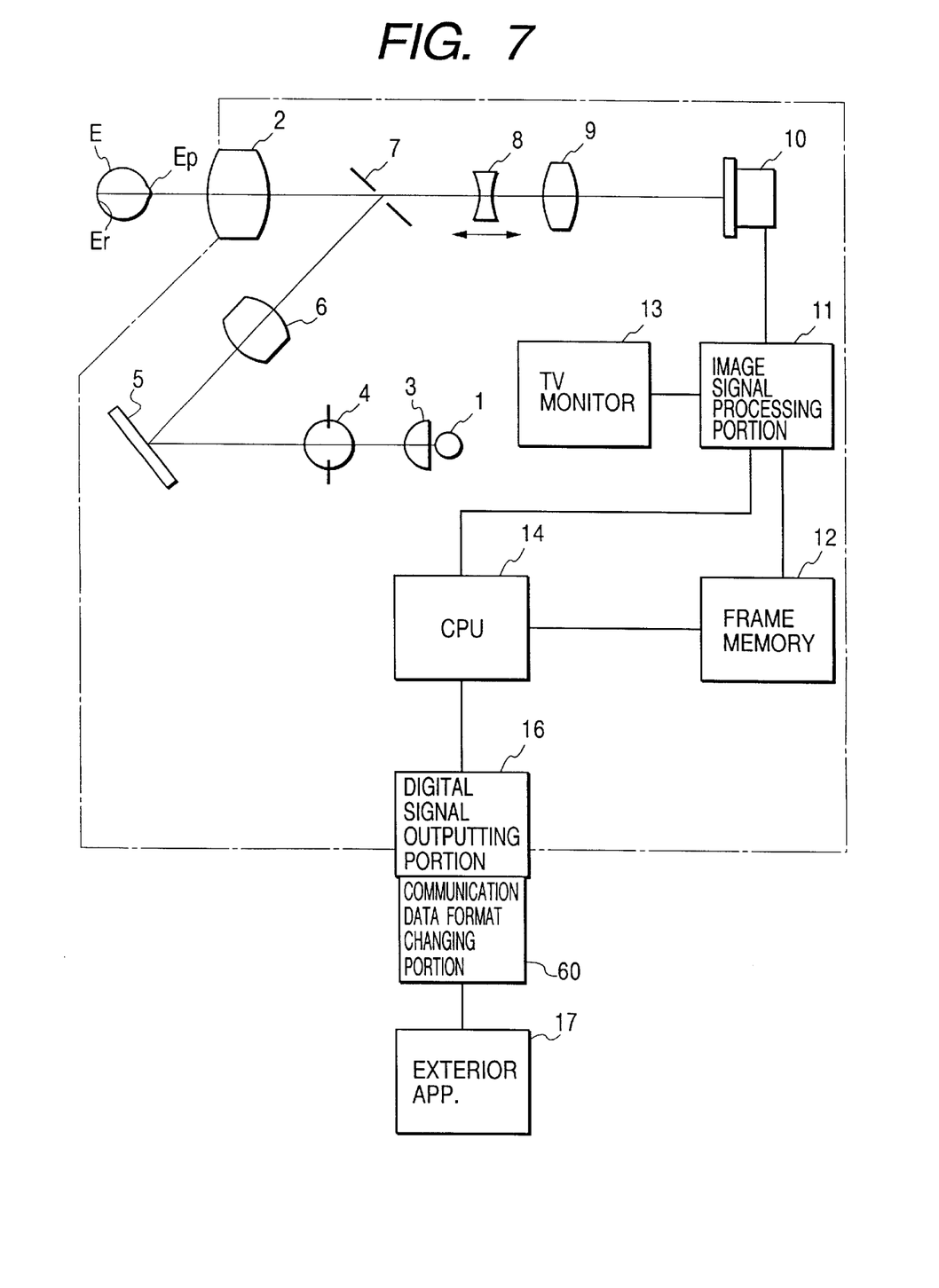
FIG. 7 shows the construction of a further embodiment of the present invention.

FIG. 7 shows the construction of a fourth embodiment of the present invention. In this embodiment, the data format selecting portion 15 of FIG. 1 is eliminated and a communication data format changing portion 60 is added to the digital signal outputting portion 16. The output of the CPU 14 is connected to the communication data format changing portion 60 through the digital signal outputting portion 16, and the output of the communication data format changing portion 60 is connected to the exterior apparatus 17.

When an image is recorded in the frame memory 12 by the phototaking operation shown in the first embodiment, the CPU 14 reads out image information from the frame memory 12 and outputs it to the digital signal outputting portion 16. The digital signal outputting portion 16 which has received the output outputs the signal intactly to the communication data format changing portion 60, which thus changes the communication speed of the inputted signal, the length of the data, the number of input and output signal lines, etc. so as to become the same as the communication format of the exterior apparatus 17.

Depending on which communication data format the exterior apparatus has for communication data formats such as SCSI, ethernet, RS-422 and RS-232C, the communication data format changing portion 60 may be automatically changed over, and communication data format selecting means may be provided in the communication data format changing portion 60 and the communication format may be changed over in conformity with the selection by this selecting means.

Also, the communication data format changing portion 60 may be removably mountable and a plurality of communication format changing portions provided in conformity with the communication formats may be made interchangeable in conformity with the exterior/apparatus 17. Further, if the communication between the digital signal outputting portion 16 and the communication data format changing portion 60 is made into a communication corresponding to PCMCIA standard, the change of the communication format can be done easily and it becomes possible to connect the apparatus to modem, a hard disc or the like easily. In this manner, the communication data format of the exterior apparatus 17 can be flexibly coped with.

As described above, provision is made of the digital signal converting means and the data format changing means for changing the data format of the output signal, whereby data processing means for exclusive use is not required of the surrounding apparatus and therefore, the apparatus of the present invention is excellent in universal use and excellent in the interchangeability of data, and the range of utilization of digital image data can be markedly widened.

Also, if selecting means for selecting the image compression rate is provided at hand, it will become possible to compress the image easily even in the course of phototaking, and the recording medium can be efficiently utilized. Further, it will become possible to set a phototaking condition using a small quantity of phototaking light in accordance with the compression rate and therefore, the quantity of light applied to the eye to be examined will be decreased and thus, the burden of the examinee can be decreased and also, by the allowed amount of focus being changed in accordance with the compression rate, the time required for focusing can be shortened.

Further, if the digital signal outputting means for outputting the output signal of the image relating information controlling means and the digital image signal is provided in common, it will be possible to prevent the discordance of data and carry out ophthalmologic phototaking of high reliability.

Also, if communication format changing means capable of changing communication data formats is provided in the output means, the operability will be improved and a wide range of surrounding apparatuses can be coped with without being affected by different data formats for digital communication possessed by a variety of diagnosis systems in a hospital, and the universal usability of the system will be improved and the system can also contribute to the diagnosis and treatment at remote places by the connection thereof the modem or the like.

What is claimed is:

1. An ophthalmologic photographing apparatus comprising:

an illuminator for illuminating an eye to be examined;

a photographing system having an image pickup device for taking images of the eye to be examined illuminated by said illuminator, said photographing system further having a signal converter coupled to said image pickup device for converting signals of said image pickup device into digital image data;

an image compressing system, having a selector, for compressing said digital image data at a desired compression rate selected by the selector;

a monitor for displaying the compressed image of the eye to be examined according to the desired compression rate and for permitting an operator to confirm the level of image deterioration due to the compression rate;

a recorder for recording the compressed digital image data; and a switch for ordering the recorder to record the digital image data, wherein the operator operates said switch to record the compressed image at the desired compression rate after selecting a desired compression rate with said selector and confirming the level of image deterioration due to the selected compression rate by viewing said monitor to view the compressed image of the eye to be examined according to the desired compression rate.

2. An apparatus according to claim 1, wherein said image compressing system executes the compression with a non-reversible image compression algorithm, and said selector comprises a switch for the operator to select the desired compression rate 1/N where N>1.

3. An ophthalmologic photographing method comprising:

illuminating an eye to be examined;

photographing images of the illuminated eye to be examined with a digital camera which outputs digital image data;

compressing said digital image data at a desired compression rate;

displaying the compressed images of the eye to be examined according to the desired compression rate, thereby permitting an operator to confirm the level of image deterioration due to the compression rate;

allowing the operator to see the compressed images and to select the compression rate; and recording the compressed digital image data.

4. A method according to claim 3, wherein said compressing step is executed with a non-reversible image compression algorithm with the desired compression rate 1/N where N>1.

* * * * *

UNITED STATES PATENT AND TRADEMARK OFFICE
CERTIFICATE OF CORRECTION

PATENT NO.   : 6,327,375 B1
DATED        : December 4, 2001
INVENTOR(S)  : Kazuhiro Matsumoto et al.

It is certified that error appears in the above-identified patent and that said Letters Patent is hereby corrected as shown below:

<u>Column 2,</u>
Line 28, "strong" should read -- resistant --

<u>Column 3,</u>
Line 37, "unit" should read -- emit --.

<u>Column 6,</u>
Lines 8 and 16, "contract" should read -- contrast --.
Line 45, "infirmation," should read -- information, --.

<u>Column 8,</u>
Line 63, "exterior/apparatus 17." should read -- exterior apparatus 17. --.

<u>Column 9,</u>
Line 39, "thereof" should read -- thereof with --.

Signed and Sealed this

Fourth Day of February, 2003

JAMES E. ROGAN
*Director of the United States Patent and Trademark Office*